United States Patent [19]

Sirotkin

[11] Patent Number: 4,959,312

[45] Date of Patent: Sep. 25, 1990

[54] FULL SPECTRUM MUTAGENESIS

[75] Inventor: Karl M. Sirotkin, Knoxville, Tenn.

[73] Assignee: The University of Tennessee Research Corporation, Knoxville, Tenn.

[21] Appl. No.: 739,962

[22] Filed: May 31, 1985

[51] Int. Cl.$^5$ ............................................. C12P 19/34
[52] U.S. Cl. ................................. 435/91; 435/172.1; 435/172.3; 935/16; 935/17
[58] Field of Search ................ 435/68, 70, 172.3, 317, 435/172.1, 91; 935/1, 16, 23, 33, 17

[56] References Cited

PUBLICATIONS

K. Sirotkin, J. Theor. Biol., Galley Proof (1986).
Zoller et al. (1982), Nucleic Acids Research, vol. 10, pp. 6487–6500.
Dalbadie-McFarland et al. (1982), *Proc. Natl. Acad. Sci. USA*, vol. 70, pp. 6409–6413.
Directed Mutagenesis, David Shortle, Ann. Rev. Genet., 15:265–294 (1981).
Fidelity of DNA Replication Under Conditions Used for Oligodeoxynucleotide-Directed Mutagenesis, Jian-Ping Shi and Alan R. Fersht, J. Mol. Biol., 177:269–278 (1984).
Oligonucleotide-Directed Mutagenesis of DNA Fragments Cloned into M13 Vectors, Mark J. Zoller and Michael Smith, Methods in Enzymology, 100:468–500 (1983).
A General Method to Select for M13 Clones Carrying Base Pair Substitution Mutants Constructed in Vitro, Cinzia Traboni et al, Nucleic Acids Research, 11:4429–4239.
Site Specific Mutagenesis: Insertion of Single Noncomplementary Nucleotides at Specific Sites by Error-Directed DNA Polymerization, Richard A. Zakour, Elizabeth James and L. A. Loeb, Nucleic Acids Research, 12:6615–6629 (1984).
Targeted Mutagenesis in Vitro: Lac Repressor Mutations Generated–Using AMV Reverse Transcriptase and dBrUTP, John E. Mott et al, Nucleic Acids Research, 12:4139–4152 (1984).
Terminal Transferase: Use in Tailing of DNA and for in Vitro Mutagenesis, Guo-Ren Deng and Ray Wu, Methods in Enzymology, 100:96–116 (1983).
Terminal Labeling and Addition of Homopolymer Tracts to Duplex DNA Fragments by Terminal Deoxynucleotidyl Transferase, Ranajit Roychoudhury et al, Nucleic Acids Research, 3:101–116 (1976).
T4 RNA Ligase as a Nucleic Acid Synthesis and Modification Reagent, Richard I. Gumport and Olke C. Uhlenbeck, Gene Amplif. Anal., 2:313–345 (1981).
The Preparative Synthesis of Oligodeoxyribonucleotides Using RNA Ligase, Deborah M. Hinton et al, Nucleic Acid Research, 10:1877–1895 (1982).
The Synthesis of Oligodeoxyribonucleotides Using RNA Ligase, Deborah Hinton and Richard I. Gumport, Nucleic Acids Research, 7:453–465 (1979).

*Primary Examiner*—Richard A. Schwartz
*Attorney, Agent, or Firm*—Luedeka, Hodges & Neely

[57] ABSTRACT

A method is disclosed for in vitro mutagenesis of a target DNA sequence which generates mutants containing a single randomly-located region in the target sequence with random substitution mutations. The method includes the production of a supply of a template for the target sequence and random primers having differing 3'—OH termini. At least two nucleotides are added randomly to the primers to produce modified random primers, some of which contain at least one mismatch with respect to the template. The modified random primers are employed with the supply of the sequence to polymerize from the 3'—OH terminus of the modified random primer along the template to biologically fix mutations resulting from mismatched bases and produce molecules having a double-stranded region containing a mutant strand. The molecules are transferred into the host organisms to cause at least some of the mutant strands to be replicated in the host organism to produce mutant DNA sequences. These organisms are grown into a population of clones each containing a mutant sequence. One or more clones are selected based on desired characteristics and a mutant sequence is amplified to produce a usable supply of the mutant sequence.

22 Claims, No Drawings

FULL SPECTRUM MUTAGENESIS

The present invention relates to in vitro mutagenesis and more particularly relates to an in vitro method for mutagenesis which produces mutants having random substitution mutations which are distributed randomly throughout a target DNA sequence.

Advances in genetic engineering have made it possible to produce known biological materials such as insulin and interferon by the transfer of genes coding for the material into appropriate microorganisms. It is now also possible to produce novel proteinaceous materials which are not found in nature using recombinant DNA technology. For example, novel enzymes for use in food processing, chemical and pharmaceutical production and environmental control are being developed. The development and production of these novel materials have been given the label "protein engineering".

Proteins, which include such diverse materials as enzymes, hormones, antibodies and albumins are made up of sequences of the 20 amino acids. In biological systems, DNA (deoxyribonucleic acid) determines the composition and order of the amino acids in a protein and the genetic unit "gene" identifies a segment of DNA which codes for a particular protein. In "protein engineering" it is necessary either to create new genes or to mutate wild-type genes which may be transferred into an organism to produce a novel material. While recombinant DNA techniques have been developed which can readily effect isolation and transfer of genes, the planned production of a specific novel gene for a desired novel material has been difficult because of the lack of full understanding of the correlation between protein structure and function. Therefore, a method is needed which efficiently generates a population of differing novel sequences from which desired novel sequences are selected. Such sequences can be transferred into host microorganisms to produce novel proteinaceous materials and to impart various desirable properties to microorganisms which are useful in other biotechnological processes. Furthermore, in a wide variety of biological studies relating to protein structure, synthesis and function such as studies of enzyme function, antibody binding, viral pathogenesis, transcription and translation, mutants with a wide variety of possible substitution mutations in a sequence are often desired.

Known in vitro mutagenesis techniques such as oligonucleotide mediated site-directed mutagenesis can be used to produce all possible substitutions in a DNA sequence but mutations at each differing site require the synthesis of a new oligonucleotide. Consequently, this technique cannot be used to efficiently produce a population of mutants each having a different region of mutation throughout the sequence. Other techniques such as chemical mutagenesis with hydroxylamine or bisulfite or mutagenesis by incorporation of base analogues can produce mutations throughout a chosen region but cannot efficiently produce all possible codon length substitution mutations in that region.

Therefore, the object of the present invention is to provide a method which produces mutants containing random substitution mutations at random sites in a DNA sequence. It is a further object to provide a method which is capable of producing all possible codon length substitution mutations in a target region. Other objects and advantages of the invention will become known by reference to the following description and examples embodying the present invention.

Generally, the present invention is an in vitro method for the alteration or "mutagenesis" of a target DNA sequence such as a gene for a protein or a fragment of such a gene, or other DNA sequence.

DNA is a double-stranded molecule containing a deoxyribose sugar, a phosphate group, and one of the four bases, adenine (A), thymine (T), cytosine (C) and guanine (G). The backbone of each strand is formed from strands of the sugar and phosphate group with a phosphodiester linkage between the 3' and 5' carbon atoms of the sugar. The strands are antiparallel and thus the paired strands extend in opposite directions, i.e. one strand extends from 3' OH to a 5' phosphate and the other extends from a 5' phosphate to a 3' OH.

"Complementary" bases of each strand join the two strands by hydrogen bonding and other interactions, i.e., T pairs with A and C pairs with G and the two strands form a double helix. While both strands of the double-stranded DNA are identified as the gene coding for a particular protein, one strand is called the "sense" strand and is usually used to identify the sequence of bases while its complement is actually transcribed to produce messenger RNA (ribonucleic acid) which is translated to form proteins.

Three bases in a particular order in the DNA, i.e., "ATC", code for one amino acid of a protein and are referred to as a codon (bases are generally stated as are present in the "sense" strand). There are 64 codons which code for the 20 amino acids and provide stop signals to terminate polypeptide chains. The genetic code is "degenerate" and more than one codon codes for the stop signals and for some amino acids.

The method of the present invention produces random substitution mutations of two or more bases in a target DNA sequence with the mutations being located in a single randomly-located region in the target sequence. The method includes the production of a supply of a template for the sequence and random primers having differing 3'-OH termini with each having a region complementary to the template adjacent the 3'-OH termini. At least two nucleotides are added randomly to the primers to produce modified random primers, some of which contain at least one mismatch with respect to the template. The modified random primers are employed with the supply of the sequence, and polymerization from the 3'-OH terminus of the modified random primer along the template biologically fixes the mutation. The resulting DNA molecules produced from modified random primers which have mismatched bases have a double-stranded region containing a mutant strand. The molecules are transferred into the host organisms to cause at least some of the mutant strands to be replicated in the host organism to produce mutant DNA sequences. These organisms are grown into a population of clones each containing a mutant sequence. One or more clones are selected based on desired characteristics and a mutant sequence is amplified to produce a supply of the mutant sequence.

The method generates "random" substitution mutations in the DNA sequence, i.e., mutations which do not occur at a particular site and which do not result in a specific base exchange and, in addition, produces a population of clones containing such mutations. Mutants are selected from the population based on desired characteristics and the mutant sequences are useful in a wide variety of biological studies and in protein engineering. Expression of mutant sequences or genes constructed from the mutant sequences in competent organisms produce novel proteinaceous materials. The method is also useful for the preparation of improved control sequences, e.g., high signal strength transcription promoters which have a wide variety of genetic engineering applications and other such sequences.

Employing the method of the present invention, it is possible to produce random mutations of two or more bases in a single region with the region of mutation being distributed throughout the target sequence. In addition, bases in the sequence can be changed to any other base. Therefore, it is possible to change codons at any and all sites in the target sequence to any other codon. With the present invention, the probabilities for mutation at all sites in the target sequence are not necessarily equal nor is the chance for the substitution of a particular base necessarily equal at each site. Consequently, "completely" random mutations may not occur when the method of the present invention is employed. It is also possible to limit the size the target sequence or to prevent the incorporation of up to three of the four bases into the sequence at a mutation with the method of the present invention. There is no intent to exclude such embodiments of the method or to limit the present invention to a method for the generation of completely random mutations by the use of the words "random" or "randomly" in this application.

For the method of the present invention, it is necessary to produce a supply of single-stranded template of the target sequence. The single-stranded template can be either the sense strand or its complement. Thus, the word "template" in this application is intended to refer to either strand.

A supply of a template for the sequence is easily produced from a supply of the sequence produced by cloning the sequence using known recombinant DNA techniques. Recombinant DNA techniques generally involve the insertion of the sequence into a phage, plasmid, or cosmid vector, which produces a recombinant DNA molecule which is then introduced into an appropriate organism, such as a bacterium, for replication. Replication of the recombinant DNA molecule vector in the organism results in replication of the target sequence. Many appropriate vectors and transfer techniques are well known and are described generally in Watson et al, *Recombinant DNA*, W. H. Freeman and Co. (1983). Specific Procedures are described in Maniatis et al, *Molecular Cloning*, Cold Spring Harbor Laboratory (1982).

For the production of the template, it is preferable for the supply of the target sequence to be carried as an insert in a DNA molecule such as a vector used to clone the sequence or other appropriate vector into which the sequence has been subcloned. The template is then generated from the vector with insert to produce molecules which retain the essential genes of the vector so that the vector will replicate following mutagenesis.

One form of the invention employs the cloning of the sequence in a single-stranded vector such as the phage vector M13 MP series or other such vectors which produce single-stranded virion DNA. The sequence is first inserted into the double-stranded relicative form (RF) of the M13 vector. Cells containing such phage vectors containing an inserted sequence bud a virion corresponding a single-stranded circular genome (virion "+" strand) which can function as a template for the sequence. Such procedures are well known and are described in J. Messing, "New M13 Vectors for Cloning" *Methods of Enzymology*, Vol. 101, Wu, R. Grossman, C., Moldive, K., Eds., Academic Press (1983). Alternately, the sequence is cloned in any appropriate vector and is subcloned into M13 or similar vector to produce a supply of the template.

Random primers for use in the method of the present invention are produced by any one of a variety of methods which produce single-stranded nucleic acid primers having differing 3'OH termini with each having a region complementary to the template at the 3'OH terminus. DNA or RNA primers are produced as are necessary for the particular enzymes employed in the method as will become apparent hereinafter.

One method for the production of random primers is polymerization initiated from a starting primer along the template. An appropriate DNA polymerase such as *E. Coli* Polymerase I, large fragment, or AMV reverse transcriptase polymerizes DNA in vitro along the template in the 5' to 3' direction from the four nucleoside triphosphates in an appropriate buffer. Since it is necessary to initiate the polymerization along the template with a starting primer when known DNA polymerases are employed, it is preferable for the template to be carried in a vector which has a known sequence adjacent the 3' end of the template such as a vector used for dideoxy sequencing, e.g., M13. For M13 and other vectors, primers are commercially available which are complementary to a sequence in the virion strand adjacent a restriction endonuclease site for insertion of foreign DNA into the vector. The commercially available primer is hybridized to the vector to serve as the starting primer and is extended into the template for the target sequence to random 3' termini to form random primers.

Randomization of 3' termini by the polymerization reaction is effected by kinetic control such as by dividing the reaction mixture into a number of aliquots and altering the reaction time for each. Also, the concentration of the polymerase can be varied for different aliquots to effect control alone or in conjunction with varied reaction times.

Control of the polymerization reaction to produce random 3'-OH endpoints is alternately accomplished by the use of appropriate concentrations of dideoxynucleoside triphosphates for each base which act as a blocking groups when incorporated and thus terminate the extension reaction along the template. The dideoxy concentration is adjusted to achieve a relatively even distribution of random 3' termini throughout the target sequence. To achieve relatively even distribution, it is believed to be desirable to adjust the concentration of the deoxy and dideoxy forms of each base so that the deoxy concentration is between about 100 and about 1000 times the dideoxy concentration. Following the extension reaction, a brief digestion with a 3' to 5' exonuclease such as Exo III is used to remove dideoxy nucleotides and further randomize the 3'-OH termini, generating random primers for use in the method.

Another method for the production of random primers involves the cleaving of DNA or RNA containing a strand complementary to the template into oligoprimers having random 3'-OH termini. DNA oligoprimers to serve as random primers are conveniently produced by cloning the sequence in a vector which is different from the vector employed in the mutagenesis. Use of a different vector results in the production of a double-stranded sequence which contains the complementary strand for the template but fragments of the vector itself will not be complementary to the vector used in mutagenesis. Partial digestion followed by denaturing yields a mixture of single-stranded fragments. This mixture will contain single-stranded fragments complementary to the template and an equal number of single-stranded fragments of the template itself. The mixture will also contain fragments of the cloning vector which will not be complementary to either the template or the stand complementary to the template.

To produce primers from double-stranded DNA containing the sequence, the partial digestion is preferably performed in a manner which maximizes the randomization of the 3'-OH termini. Reaction with a deoxyribonuclease with little sequence specificity is preferred. For example, a deoxyribonuclease such as pancreatic DNase I in an appropriate concentration may be used to cleave double-stranded DNA at random locations. It is preferable, however, to adjust the reaction time and concentration of the deoxyribonuclease to result in the maximum yield of the appropriate size fragments and to minimize any sequence preference of the deoxyribonuclease. The double-stranded fragments so produced are denatured and are size-selected and hybridization-selected to produce primers of an appropriate size and purity and will be described in more detail hereinafter.

With a single-stranded phage vector, such as M13, it is convenient to use the same vector to produce the complementary sequence for the production of DNA oligoprimers. To accomplish this, insertion of the sequence into the RF is performed so that the sequence is inserted in both orientations. Preferably, this is accomplished by cloning the target sequence in a vector and then subcloning into M13. In one orientation, one strand of the double-stranded sequence to will be in the "+" (virion) strand with its complementary strand in the "−" (nonvirion strand) and in the other orientation the complementary strand will be in the + virion strand. This is accomplished by employing the same restriction endonuclease for cleaving M13 RF and to produce like cohesive ends on the insert sequence containing the target sequence. Alternately, orientation can be forced using two different nucleases for cleaving the sequence and pairs of related vectors such as M13 mp 8 and M13 mp 9. Because the polylinker regions of mp 8 and mp 9 have the same pairs of endonuclease sites but in opposite orientations in the polylinker, the same fragment will be in opposite orientation in the two vectors. To generate a supply of the complementary sequence, vectors containing the virion strand complementary to the template are isolated and propagated. Digestion of this recombinant virion DNA produces fragments which are complimentary to the template in the vector but fragments from the vector itself will not be complementary because they are fragments of the same virion strand.

To produce primers from single-stranded DNA containing a sequence complementary to the template such as M13, a nuclease which has little site-specificity such as Nuclease S1 is used to partially digest the single-stranded material to produce random primer fragments. These fragments are size and hybridization selected according to the procedures to be described to produce primers of a selected size and purity.

Depending on the desired nature of the mutants resulting from the method, heat and alkaline conditions may also be used to digest single or double-stranded DNA into fragments. This method is suitable when it is desirable to have primers which terminate at the 3' terminus with guanine or adenine, since digestion by this method results in cleavage more frequently at these sites. It is possible to decrease preference for guanine and adenine following alkaline digestion with brief a exonuclease digestion to remove nucleotides randomly from the 3' terminus.

RNA suitable for cleavage into random RNA primers is conveniently by any of the known methods for the transcription of DNA to produce RNA which will hybridize to the template. A particularly convenient method employs a commercially available SP6 transcription system which is easily set up by use of a commercially available kit such as the kit sold by New England Nuclear of Boston, Mass. Another such kit is based on T7 and is sold under the trademark Genescribe by U.S. Biochemical Corp. of Cleveland, Ohio. With such transcription systems, a template of the target sequence is transferred into a specially constructed vector between a transcription promoter sequence for an RNA polymerase utilized in the system and a termination sequence. The RNA polymerase is employed in an appropriate buffer with the four ribonucleoside 5' triphosphates. These systems are capable of generating milligram amounts of RNA starting from as little as microgram amounts of template DNA.

Following cleavage of nucleic acids to produce random primer fragments, size and hybridization selection of the random primer fragments is preferably performed to select oligoprimers which are complementary to and which are sufficiently long to anneal to the template and form sufficiently stable hybrids so as not to disassociate when employed in the method of the present invention. The procedures for size selection are generally the same for both DNA and RNA primers and a wide variety of known techniques can be used. For example, preparative acrylamide gel electrophoresis can be used to select fragments of a particular size which can be concentrated by lyophilization. The concentrate can be desalted on filters such as those sold under the trademarks Sephadex G50, G25 or G15 by Sigma of St. Louis, Mo. followed by vacuum concentration. Alternately, other methods such as high pressure liquid chromatography or affinity chromatography are used for size selection.

Hybridization selection is easily accomplished by filter binding techniques. Nucleic acids which are complementary to the the primer nucleic acids are bound to a nylon or nitrocellulose filter which is placed in contact with the size-selected fragments. The stringency of the hybridization conditions is adjusted to select fragments which are homologous and which are sufficiently large as required by the method. Complementary fragments hybridize to the DNA on filter and are eluted from the filter following washing to remove non-hybridized nucleic acids. Nucleic acids for use in hybridization selection can be any DNA or RNA which hybridizes to the random primer fragments. Suitable DNA is the template DNA such as that prepared for use in the method. When the template is cloned in M13, the recombinant virion DNA is preferably used for the hybridization since it can be used directly without denaturation or additional preparation.

Primers and templates for use in the present invention are also simultaneously produced by the digestion of double-stranded DNA containing the sequence. For example, a suitable procedure is disclosed P. Abarzua et al., Proc. Natl. Acad. Sci., U.S.A., 81: 2030 (1984). The sequence is cloned in the double-stranded RF of an appropriate phage vector. A restriction endonuclease is used to cleave the circular RF near or within the insert. The linear molecule so produced is used as a substrate for Exo III digestion in an appropriate buffer. Aliquots are removed sequentially and the digestion is terminated in each aliquot. The aliquots are pooled and the digestion products are denatured. Hybridization with single-stranded circular virion DNA containing the template for the sequence yields gapped circular DNA molecules with a primer having a 3'—OH terminus along the template. Because the 3'—OH termini of primers in different molecules are randomly distributed within the template region, this method is suitable for the production of a template and random primers to be employed in the present invention.

Another method for the simultaneous generation of the template and random primers employs a double-stranded vector in which the sequence has been cloned and RNA complementary to one strand of the sequence to anneal to the template and displace the other DNA strand. The displaced region is susceptible to digestion with a single-strand specific nuclease such as nuclease S1 and mild S1 digestion results in one nick which produces a gap when enlarged by digestion with Exo III or two or more nicks which produce a gap which is enlarged by digestion with Exo III. RNA suitable for the displacement is generated in a transcription system into which the target sequence has been transferred such as SP6 or a transcription system based on phage T7. An appropriate buffer is employed during annealing which preferentially promotes the formation of RNA-DNA duplexes.

In this alternative, the digestion with the single-strand specific nuclease is preferably performed to cause, on the average, only one nick to be formed at a random location in the displaced region. During the digestion it is preferable to protect any single-stranded regions in the vector which could be digested and thus destroy the vector. For example, if the sequence is cloned in phage lambda it is preferable before annealing the RNA to anneal and ligate lambda DNA so that the COS sites are protected and digestion does not occur at those areas. Gapped molecules result with a 3'—OH terminus at one end of the gap and thus function as random primers which are randomly distributed throughout the target sequence in different molecules.

In the method of the present invention, the random primers are extended by the random addition of at least two nucleotides. The nucleotides are added randomly without any necessary correspondence to the complementary base at the corresponding position in the template. Random addition produces modified random primers, at least some of which by chance contain mismatched regions with respect to the template.

In the preferred form of the present invention terminal deoxynucleotidal transferase (TdT) is used to add nucleotides to the random primers before the random primers are annealed to the template. To use terminal transferase for random addition of any of the four nucleotides, it is necessary for all four nucleoside 5' triphosphates to be present in an appropriate buffer system in appropriate concentrations such that random addition occurs. However, other concentrations or conditions may be desirable to promote addition which is not completely random as desired. For example, one or more nucleoside triphosphates may be omitted to obtain a desired result.

The terminal transferase reaction should generally be carried out at about 37° C. and the pH of the buffer should be between about 6.9 and about 7.0 and contain $Mg^{2+}$ or $Co^{2+}$. The terminal transferase reaction is preferably controlled kinetically by limiting reaction time. The concentration of sodium chloride in the buffer may be also used to adjust the reaction rate. When kinetic control is employed or when the primers are dissociated from the template. $Mg^{2+}$ is the preferred divalent cation. Generally, it is necessary to calibrate the terminal transferase reaction prior to addition or when a new supply of terminal transferase is employed using a reference primer and under similar conditions to insure that reaction times and concentrations result in the addition of the desired number of nucleotides.

Alternately, the reaction is controlled by the presence of termination groups such as dideoxynucleoside 5'-triphosphates or deoxynucleoside 5' triphosphates having a 3' phosphate group. The addition reaction controlled with blocking groups is followed by a brief *E. Coli* Exo I or Exo VII digestion to remove the dideoxy nucleotide. When Exo I is used, an alkaline phosphatase digestion is necessary to remove the 3' phosphate group which remains after Exo I digestion. Another control method employs both dideoxy nucleotide and $\alpha$ thio-analogues. The reaction using terminal transferase incorporates $\alpha$ thio-analogues randomly and is terminated by dideoxy addition. Reaction with *E. Coli* Exo I removes the dideoxy group and continues removing other nucleotide until a $\alpha$ thio-analogue is reached. The $\alpha$ thio-analogue thus forms the 3' terminus.

The number of nucleotides added according to the present invention is determined by the nature of the mutation desired and by the means employed for biological fixation of the mutuation. It is preferable to limit the maximum number of nucleotides added so that frame shifts, which are more likely with longer extensions, are controlled at a level which is acceptable for the application of the method. In the preferred form of biological fixation employing AMV reverse transcriptase as will be described, it is believed preferable for the terminating nucleotide added to match the template for extension along the template for efficient biological fixation. Thus, n+1 nucleotides are preferably added for a maximum of n nucleotides to be changed. To illustrate, if it is desired to introduce a mutation containing a maximum of three altered bases, four nucleotides are added randomly. One fourth of the addition products will by chance have a matching nucleotide at the terminal position and will undergo efficient biological fixation. Therefore, mismatched nucleotides not at the terminal position result in the efficient production of substitution mutation having a length up to the number of nucleotides (n). Of course, because some of the n number of nucleotides will by chance match the template, mutations will usually not result in a mutation of maximum length. No mutation will result if no mismatched bases are introduced. It will also be understood that the number of nucleotides to be added is a target or average number to be added and that the number of nucleotides added may vary between molecules depending on the method employed to add nucleotides.

In order to make the number of nucleotides added essentially uniform for all of the modified random primers, another form of the present invention employs the joining of random oligomers of a known length to the random primers to effect the extension of at least two nucleotides. This is accomplished with a ligase capable of ligating the oligomer to the 3' terminus of the primer, such as T4 RNA ligase. In such reactions, the oligomer has a 5' phosphate and is referred to as a "donor" and the primer providing a 3'—OH terminus is referred to as an "acceptor". With RNA ligase, it is preferable for the primer (acceptor) to be RNA but DNA may also be used provided that its length is sufficiently short to provide a high concentration of ends. Preferably, DNA donor oligomers are employed because it is believed that DNA oligomers are most effective for producing modified random primers although RNA oligomers can also be used under appropriate conditions.

In this form of the invention using RNA ligase, the donor oligomers preferably have the following structure:

$$(Np)_i(B)\text{-}3'$$

B represents a blocking group in RNA oligomers such as an thio-analogue or a 3'-phosphate so that only one addition occurs for each primer. "Np" represents ribonucleotides or deoxyribonucleotides. "i" represents the number of nucleotides and ranges between 3-11 and preferably ranges between 4 and 5. When DNA donors are employed, a blocking group is usually not required since DNA is not an effective acceptor with RNA ligase and multiple ligations will rarely result. The donor oligomers are prepared in any suitable manner but preferably are chemically synthesized. It is possible for the donors to be formed with random sequences with all possibilities present or for certain mutations to be targeted by the planned presence of certain sequences in the donor. Adenosine triphosphate (ATP) is necessary in the addition reaction and thus a suitable buffer for the RNA ligase reaction must contain an appropriate concentration of ATP necessary for efficient reaction.

Biological fixation of the mutation is accomplished by employing the modified random primers with the supply of the template for polymerization along the template.

The polymerization must be conducted so that the mismatched region of the modified random primers are not "edited" to make the region correspond to the template which would reverse the mutation. The preferred form of the invention employs AMV reverse transcriptase (AMV RT) since this enzyme lacks the 3' to 5' exonuclease editing activity and thus may be used to extend the modified random primers which contain a mismatch with respect to the template. As described previously, it is preferable for at least one matching nucleotide to be present at the 3' end of the modified random primer. In addition, it has been observed that a faster reaction results if two or more nucleotides match at the terminal end of the modified random primer.

It is believed to be possible to add α thio-analogues to produce the modified random primers since thio-analogues are not usually removed by the 3' to 5' editing capacity of DNA polymerases. Other polymerases which have the 3' to 5' editing capacity such as the Klenow fragment of *E. Coli* Polymerase I can then be employed in the method.

The polymerization along the template results in DNA molecules some of which have a double-stranded region containing at least one nucleotide which is mismatched with respect to the template. These molecules or at least the double-stranded region of the molecules are transferred into an appropriate host so that the mutant strands are replicated to result in mutant DNA sequence. Methods for transfer into an appropriate host include any of the known methods including transformation, transfection, in vitro packaging followed by infection or any suitable other method for the transfer of DNA into a host.

In the preferred form of the invention where the template is in M13, transfer of the sequence into a host is accomplished by generating the RF of M13 which is used to transform a bacterial host. The term "RF" as used in this application is intended to refer to the double-stranded form of single-stranded vector DNA, regardless of whether or not it is supercoiled. The RF is generated by continuing the polymerization around the virion strand and sealing the nick at the primer. Extension around a single stranded molecule to the random primer can be accomplished with AMV RTase and the nick sealed with a DNA ligase such as T4 ligase. Most preferably, AMV RTase is used for partial extension followed by continued polymerization with a DNA polymerase, T4 DNA polymerase being preferred.

Using RNA primers, biological fixation requires additional steps after partial extension to produce DNA containing the mutation. Also, the partial extension should extend at least through the target sequence to a "reverse sequencing primer" region in the vector. A DNA complement strand is thus easily generated which is complementary to the initial extension product. Preferably, this is accomplished by disassociating the initial extension product and annealing a "reverse sequencing primer" to the initial extension product. Reverse sequencing primers are commercially available for M13 and other vectors such as the M13 reverse sequencing primer available from Pharmecia P-L Biochemicals of Piscataway, N.J. Extension from the reverse sequencing primer with a DNA polymerase capable of employing RNA as a template such as AMV reverse transcriptase yields a DNA complement strand which reflects the substitution mutation generated by the method of the present invention. Then, the complement strand which has been disassociated from the initial extension product is annealed to an appropriate vector which includes both the sequencing primer and reverse sequencing primer regions. It is necessary for this vector to be cleaved between the sequencing primer and reverse sequencing primer regions and the vector to be dissociated. For example, the ends of one strand of Eco RI cleaved M13 and mp2 RF will anneal under appropriate hybridization condition of the complement strand which has, at its termini, sequences complementary to the primer and identical to the reverse sequencing primer and produce a circular molecule with double-stranded and single-stranded regions. Polymerization with an appropriate DNA polymerase followed by reaction with a DNA ligase is used to generate the double-stranded RF form of M13 from the molecule. Using this form of the present invention, the resulting double-stranded mutant sequence does not contain a region of mismatch.

The mutant sequences are introduced into a competent host organism for expression of the mutant sequence and organisms with a desired phenotype are selected. Host organisms include both prokaryotes and eukaryotes. In the preferred from of the present invention employing M13 or other single stranded phage vectors, introduction is performed by transfection into a procaryotic organism such as the bacterium *E. Coli* by known procedures.

It is desirable to employ procedures for the method of the present invention which increase the yield of mutants in the host and prevent loss of the mutant sequences upon introduction into the host. In the preferred form of the invention using E. Coli and M13 and where the molecules being introduced contain a region of mismatch, loss of the mutant sequence is preferably prevented by using M13 to generate a template for the sequence in a strain of E. Coli which is dut$^-$ and ung$^-$ so that the virion DNA and template contain some uracil instead of thymine. Because of the presence of uracil, uracil-specific nucleases will destroy virion DNA without a complete second strand which otherwise could lower the frequency of mutants. Additionally, while the strand containing the mutation sometimes will fortuitously be used as a template for repair of the template strand, it is believed the presence of uracil causes the mismatch repair machinery of E. Coli to preferentially repair the template strand to match the strand containing the mutation since the template strand containing uracil would appear to be a newly synthesized strand where the uracil has not yet been replaced by uracil excision repair enzymes.

The mutant sequence can also be subcloned into other vectors as needed for introduction into a host. The mutant sequence can be spliced to one or more other DNA sequences e.g., gene fragments, control sequences, etc., as desired to produce a gene or other genetic unit.

Following transfer of the sequences into the host, the host organisms are cultured in appropriate media according to any of a variety of known procedures to produce a population of clones containing mutant sequences and mutants containing sequences having desired characteristics are selected. After culturing is performed, discrete plaques, colonies, or other identifiable unit of clones are produced which are identifiable during selection.

Selection is suitably performed by using known techniques for the selection of microorganisms where growth either on a particular nutrient or toxic material is observed, or by histochemical selection or immunological selection where a product of the mutants sequence is detected. Any suitable selection scheme can be employed which is capable of detecting mutants with desired characteristics and a suitable number of rounds are employed to identify such mutants.

In order to obtain a usable supply of the selected mutant sequences, the method further includes the amplification of the mutant sequences. For example, this is accomplished by further culturing of the selected host organisms. In addition, mutant sequences can be subcloned into other vectors for amplification in the same or other hosts. Alternately, following selection, the mutant DNA is sequenced to determine sequence information descriptive of the mutation. Based on the sequence information, the supply of the sequence is produced using a method for producing a specific mutation such as oligonucleotide-directed mutagenesis or other such method and amplifying to produce a supply of the sequence. Amplification is again accomplished by transfer into an appropriate host and growing to produce a supply of the sequence.

The following are specific examples of methods employing features of the present invention.

EXAMPLE I

The method is employed for random in vitro mutagenesis of the M13 and mp9 polylinker with the extension of random primers being performed with terminal transferase under kinetic control.

M13 mp9 is propagated on E. Coli K12 JM103. Virions are separated from lysed cells by centrifugation to pelletize cellular debris and virions are precipitated from supernatant fluids with polyethylene glycol and NaCl. Virion DNA is purified from virions by phenol-chloroform extraction and ethanol precipitation and the DNA is resuspended in 10 mM TRIS-Cl pH 7.9 and 1 mM EDTA to result in a concentration of 500 µg/ml virion DNA.

A 17 mer sequencing primer (Pharmecia P-L Biochemicals of Piscataway, N.J.) is annealed to the M13 mp9 virion DNA in 150 mM NaCl, 10 mM TRIS-Cl pH 7.9, 1 mM EDTA with the concentration M13 mp9 virion DNA being 150 µg/ml and with the concentration of the sequencing primer being 500 ng/ml at 55° C. for 15 minutes. The solution is allowed to equilibrate to room temperature over approximately one hour. The solution containing the virion DNA and annealed primer is diluted five-fold with an appropriate buffer to result in a solution containing 30 mM NaCl 7 mM $Mg^{2+}$, 0.2 mM EDTA, 20 mM TRIS-Cl pH 7.9, and 30 µg/ml virion DNA and 100 ng/ml primer.

Sufficient quantities of each of the four nucleoside triphosphates is added to result in 1 mM of each. 100 units/ml of Klenow fragment (Boehringer Mannheim Biochemicals, Indianapolis, Ind.) is added. The solution is incubated at 37° for five minutes. 500 units/ml of Hin dIII is added to cleave, and after 30 minutes, EDTA to 20 mM is added to stop the reaction. Preparative acrylamide-urea gel electrophoresis after disassociation is used to separate a 48 base polylinker sequence ("—" strand) which is identified in Table A.

The 48 base fragment is desalted by passage through a Sephadex G-50 column (Sigma, St. Louis, Mo.) in $H_2O$. The fragment is detected in column eluant fractions by fluorescence in the presence of ethidium bromide at a concentration of 0.5 µg/ml of column eluant. Fractions containing the fragment are lyophilized and the Fragment is reconstituted to a concentration of 50 µg/ml in $H_2O$.

The reconstituted 48 base fragment in $H_2O$ is annealed to the previously prepared and purified mp9 virion DNA in a buffer containing 90 mM NaCl, 10 mM TRIS-Cl pH 7.9, 5 mM $MgCl_2$, and 10 mM dithiothreitol with the concentrations of the 48 base fragment being approximately 500 ng/ml and the M13 mp9 virion DNA being 150 µg/ml for 15 minutes at 55° C. and is allowed to equilibrate for one hour to 23° C. 1000 units/ml E. Coli exonuclease III (Exo III) (Pharmecia P-L Biochemicals, Piscataway, N.J.) is added and 12 aliquots are removed over a 4 minute period and EDTA to 20 mM is added to each aliquot upon removal to terminate Exo III digestion. The aliquots are pooled. A solution containing random primer fragments having approximately 17–48 bases is obtained by preparative gel electrophoresis after dissociation through a short agarose column followed by concentration by lyophilization and desalting through a Sephadex G-50 column (Sigma, St. Louis, Mo.) in $H_2O$ followed by a second lyophilization.

The lyophilized solution containing the random primers is added to sufficient buffer pH 6.9 containing 100 mM NaCl, 100 mM K-cocodylate, 25 mM TRIS (base), 10 mM MgCl₂, 2 mM dithiothreitol so that the random primer DNA has a concentration of about 100 ng/μl. The four nucleoside triphosphates are added to result in the following concentrations:

100 μM dGTP

100 μM dATP

500 μM dTTP 1 mM dCTP 2700 units/ml terminal deoxynucleotidyl transferase (TdT) (Pharmecia P-L Biochemicals, Piscataway, N.J.) which is calibrated to add 4-5 nucleotides with a sequencing primer as a substrate, is added and the solution is incubated for 7.5 minutes at 37° C. and the TdT is inactivated by submersion of the tube in boiling H₂O for 3-8 minutes.

M13 mp9 virion DNA is added to achieve a concentration of 800 μg/ml and the NaCl concentration is increased to 110 mM. The TdT-extended primers are allowed to anneal to the virion DNA at 55° C. for 15 minutes and then is allowed to cool to room temperature over 1-2 hours.

Following annealing, the solution is diluted five-fold and a buffer is added to result in 50 mM TRIS-Cl pH 7.6, 10 mM MgCl₂, 50 mM KCl, 20 mM dithiothreitol. All four nucleoside triphosphates are added to produce 1 mM concentrations and 1000 units/ml AMV reverse transcriptase (Seikagaku America, St. Petersburg, Fla.), which is calibrated to insure that poly-T additions of four and five nucleotides to a 17 mer sequencing primer (Pharmecia P-L Biochemicals, Piscataway, N.J.) are extended when annealed to mp9, is added and the solution is incubated for 2 hours at 37° C. A phenol extraction and ethanol precipitation is performed and the precipitated DNA is resuspended (1 μg virion DNA/50 μl) in 2 mM dithiothreitol, 20 mM Hepes pH 7.9, 10 mM MgCl₂, 500 μM dATP, 500 μM CTP, 500 μM GTP, 500 μM TTP, and 0.5 units/50 μl T4 DNA polymerase (Pharmecia P-L Biochemicals, Piscataway, N.J.). The solution is heated to 37° and the polymerization is continued for 15 minutes. Then, 5 additional units/50 μl T4 DNA polymerase and 5 units/50 μl T4 DNA Ligase (New England Biolabs, Beveraly, Mass.), rATP to 200 μM and additional equal concentrations of the four nucleoside triphosphates are added. Polymerization and ligation is continued for 75 minutes at 37° C. EDTA to a concentration 15 mM is added to terminate the reaction.

The solution is employed directly to transform E. Coli K12 DH1 competent cells (BRL, Bethesda, Md.) in a liquid suspension. An aliquot of the suspension is plated onto a lawn of E. Coli K12 JM107 and plaques observed to measure transformation efficiency. The remainder is added to a 1:100 dilution of E. Coli K12 JM107 and is cultured for 8 hours for amplification. The replicative form (RF) of the M13 mp9 is purified from the cells of the amplified culture by alkaline lysis including an ethanol precipitation. The precipitated DNA is resuspended and individual aliquots are subjected to digestion with the restriction endonucleases identified in Table 1. Cultures are kept separate and identified as to the restriction endonuclease used. Digested aliquots are used to retransform E. Coli K12 DH1 (BRL) is performed previously. RF is again isolated from the separate amplified cultures. Separate transformations are again performed. This time, no large scale amplification is performed because individual plaques are to be tested.

2 ml cultures are grown from observed plaques. RF purified from the cells of the 2 ml cultures are again subjected to digestion with the restriction endonucleases used previously and set forth in Table I. Each RF is only digested with the restriction nuclease used originally and identified with the previous transformation.

Virion DNA from virions in the supernatant fluid from cultures which are resistant to cleavage is sequenced employing Sanger (dideoxy) sequencing to identify the mutants shown in Table I. DNA sequence data given is for the sense (non-transcribed) strand with reference to the predicted lac transcript. Predicted amino acids for that transcript are also shown.

All mutations are confined to the target sequence except 1 in 50 sequenced mutants shows an additional base pair change in the 3' direction believed to be due to the relatively high mutation rate caused by AMV RT. These exceptional mutations are not shown in Table 1.

TABLE A

EXAMPLE I

3'-ACCGACGTCCAGCTGCCTAGGGGCCCTTAAGTGACCGGCAGCAAAATG-5'

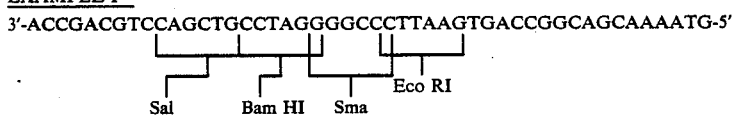

Sal   Bam HI   Sma   Eco RI

EXAMPLE II

3'-ACCGACGTCCAGCTGCCTAGGGGCCCTTAA

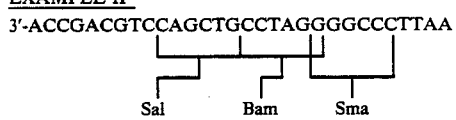

Sal   Bam   Sma

EXAMPLE III

3'-GGGCCCCTAGG CAGCTGGACGTCGGTTCGAACCGTGACCGGCAGCAAAATGTTGCAGCACTGACCC-5'

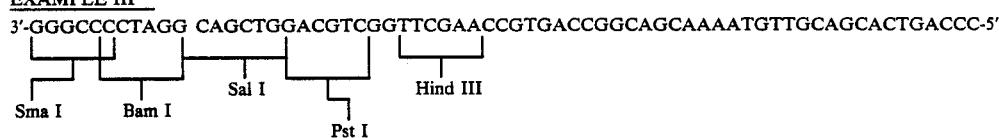

Sma I   Bam I   Sal I   Hind III
                        Pst I

EXAMPLE IV

TABLE A-continued

Same as Example III.

TABLE I

Sal-Resistant Mutants

Starting Sequence: Sal
```
GCA GGT CGA CGG ATC
ala gly arg arg ile
```

Mutant 1:
```
         *
GCA GGT AGA CGG ATC
         └─┘
         (silent)
```

Mutant 2:
```
     *   *
GCA GGA GGA TGG ATC
     gly     trp
```

Mutant 3:
```
         * *
GCA GGT CTT CGG ATC
         val
```

Mutant 4:
```
     * *
GCA AAT CGA CGG ATC
     asn
```

Mutant 5:
```
         * *
GCA GGT GAA CGG ATC
         glu
```

Mutant 6:
```
         *
GCA GGT GGA CGG ATC
         gly
```

Mutant 7:
```
             * * *
GCA GGT CGA AAT ATC
             asn
```

Mutant 8:
```
* * * *
GTC TTA CGA CGG ATC
val leu
```

BamHI-Resistant Mutants

Starting Sequence: Bam HI
```
GGT CGA CGG ATC CCC GGG AAT
gly arg arg ile pro gly asn
```

Mutant 1:
```
         * * * *
GGT CGA CGA GCT CCC GGG AAT
             └─┘ ala
             (silent)
```

Mutant 2:
```
             *
GGT CGA CGG GTC CCC GGG AAT
             val
```

Mutant 3:
```
             * *
GGT CGA CGG GTT CCC GGG AAT
             val
```

Mutant 4:
```
     * o o*  * * * * * * *
GGT CGA GAA TGC GCC CGG GAT...
     glu cys ala arg asp ...
```

Mutant 5:
```
             * * *
GGT CGA CGG AAA GCC CGG AAT
             lys ala
```

Mutant 6:
```
 * * * * *
GCA TTG TGG ATC CCC GGG AAT
ala leu trp
```

Sma-Resistant Mutants

Starting Sequence: Sma
```
CGG ATC CCC GGG AAT TCA
arg ile pro gly asn ser
```

Mutant 1:
```
             o o* * ─── ───
CGG ATC CCG GTT ATT CAC...
             arg val ile his ...
```

Mutant 2:
```
         *   * *
CGG ATC CTC TTG AAT TCA
         leu leu
```

Mutant 3:
```
         * * * *
CGG ATC AAG CGG AAT TCA
         lys ser
```

Mutant 4:
```
         * * *   o++o++
CGG ATC CCA AAG GAA TTC...
         └─┘ lys glu phe ...
         (silent)
```

Mutant 5:
```
             *
CGG ATC CCT GGG AAT TCA
             └─┘
             (silent)
```

Mutant 6:
```
             *
CGG ATC CCA GGG AAT TCA
             └─┘
             (silent)
```

Eco RI-Resistant Mutants

Starting Sequence: Eco RI
```
CCC GGG AAT TCA CTG GCC
pro gly asn ser leu ala
```

Mutant 1:
```
         *
CCC GGG TAT TCA CTG GCC
         tyr
```

Mutant 2:
```
         * * *
CCC GGG GGC TCA CTG GCC
         glu
```

Mutant 3:
```
         * *
CCC GGG GAG TCA CTG GCC
         glu
```

Mutant 4:
```
         * * * *
CCC GGG AAA GAC CTG GCC
         lys asp
```

Mutant 5:
```
             *
CCC GGG AAT ACA CTG GCC
             thr
```

Mutant 6:
```
         * * *
CCC GGG AGA CCA CTG GCC
         arg pro
```

Mutant 7:
```
         * *
CCC GGG GTT TCA CTG GCC
         val
```

---
\* change (substitution)  
\+ change due to insertion  
\- Change due to deletion  
o cannot distinguish between "*", "+", or "−"

EXAMPLE II

The method is employed as in Example I for in vitro mutagenesis of the M13 mp9 polylinker except that random oligoprimers for use in the method are prepared by DNase I cleavage of the sequence cloned in pBR322.

M13 mp9 polylinker, Eco RI-Hin dIII fragment as shown in Table A, is cloned in pBR322 Eco RI-Hin dIII sites, replacing the Eco RI-Hin dIII fragment in pBR322. Recombinant pBR322 with insert is mixed with a buffer containing 10 mM TRIS-Cl pH 7.9 and 5 mM MgCl$_2$ to result in approximately 1 mg/µl concentration of DNA. DNase I is added to 10 mg/ml and reaction is continued at 37° C. for 30 minutes. The reaction is terminated by the addition of EDTA to 20 mM. A phenol-chloroform extraction, chloroform extraction and ethanol precipitation are performed. The pellet is resuspended in Eco RI digestion buffer as per manufacturer's recommendations and digested with 1000 units/ml for 3 hours. The reaction is again terminated by EDTA to 20 ml.

The reaction mixture is subjected to preparative acrylamide gel electrophoresis and bands containing fragments which have a size of less than 48 base pairs are collected and pooled.

A solution containing the collected fragments are denatured and are contacted with a nylon filter cut into squares with 0.5 cm sides in a buffer containing 100 mM TRIS-Cl pH 7.9, 5 mM EDTA, 100 mM NaCl for 2 hours at 50° C. to which M13 mp9 virion DNA has been bound by UV. The buffer is cooled over 3 hours to room temperature. The filter is washed with the same buffer as above. Filter fragments are centrifuged in 0.5 ml micro tubes with a 26 gage needle hole in the bottom with these tubes being contained in 1.5 ml microfuge tubes to remove excess buffer. Hybridized fragments are disassociated from the DNA on the filter with excess H$_2$O at 50° C., are lyophilized, are repurified over G-50 (Sigma, St. Louis, Mo.), relyophilized and are added to the buffer as in Example I for the terminal transferase reaction.

Procedures as described in Example I are used to select restriction endonuclease resistant mutants as identified in Table II. The amino acids indicated are predicted from the sequences. DNA sequence data given is for the sense (non-transcribed) strand with reference to the predicted lac transcript. Predicted amino acids for that transcript are also shown.

TABLE II

Sal-Resistant Mutants

Starting Sequence — Sal
```
GCA GGT CGA CGG ATC
aln gly arg arg ile
```

Mutant 1
```
* * * *
GGG AAT CGA CGG ATC
gly asn
```

Mutant 2
```
      *
GCA GGT TGA CGG ATC
         (stop)
```

Mutant 3
```
          *
GCA GGT CGC CGG ATC
         (silent)
```

Mutant 4
```
          * *
GCA GGT CGA TAG ATC
              stop
```

Mutant 5
```
*   * * *    * *
GCA GGA TCG CCA ATC
        ser  pro
       (silent)
```

Pst I-Resistant Mutants

Starting Sequence — Pst I
```
AGC TTG GCT GCA GGT CGA
ser leu ala ala gly arg
```

Mutant 1
```
         *
AGC TTG GTT GCA GGT CGA
        val
```

Mutant 2
```
             *
AGC TTG GCT ACA GGT CGA
            thr
```

Mutant 3
```
             *
AGC TTG GCT GGA GGT CGA
            gly
```

Mutant 4
```
         *      *
AGC TTG GGT GCT GGT CGA
        gly   (silent)
```

Mutant 5
```
         *  *
AGC TTG GAT CCA GGT CGA
        asp
```

Mutant 6
```
         * * *
AGC TTG CAC GCA GGT CGA
        his
```

Hind III-Resistant Mutants

Starting Sequence — Hind III
```
ACG CCA AGC TTG GCT
thr pro ser leu ala
```

Mutant 1
```
     * * *
ACG CCC GGA TTG GCT
        gly
       (silent)
```

Mutant 2
```
     * * *    *
ACG TGC AGT TTG GCT
    cys  (silent)
```

Mutant 3
```
     *   * * *
ACG GCA AGC AAC ACT
    ala     asn thr
```

Mutant 4
```
         *
ACG CCA AAC TTG GCT
        lys
```

* change (substitution)
+ change due to insertion
− Change due to deletion
o cannot distinguish between "*", "+", or "−"

EXAMPLE III

The method is employed for in vitro mutagenesis of the M13 mp8 polylinker with the extension of the random primers being performed with terminal transferase under dideoxy control.

M13 mp8 is propagated and virion DNA is purified according to the procedures described in Example I. As in Example 1, a 66 base sequence complementary to the mp8 virion DNA as shown in Table A is prepared by polymerization from a 15 mer sequencing primer, TTAAGGCCCCTAGGC (Pharmecia P-L Biochemicals, Piscataway, N.J.) followed by Eco RI cleavage:

Digestion with Exo III is again used to produce random primers also as in Example I which are size selected to have a range of between 17–58 bases.

The size-selected fragments are added to a concentration of 20 μg/ml virion DNA to a buffer containing 100 mM NaCl, 100 mM K-cocodylate, 25 mM TRIS-Cl pH 7.9, 10 mM $MgCl_2$, and 2 mM dithiothreitol. The four deoxynucleoside triphosphates and dideoxycytosine nucleoside triphosphate are added in sufficient amounts to achieve the following concentrations:

| | |
|---|---|
| 100 μM dGTP | 50 μM ddCTP |
| 100 μM dATP | |
| 500 μM dTTP | |
| 1 mM dCTP | |

Following incubation for 20 minutes, the TdT is inactivated by submersion of the tube in boiling $H_2O$. After allowing the solution to cool to 55° C., 0.001 unit Exo VII (BRL, Bethesda, Md.) are added to the solution and a very brief digestion of approximately 5 minutes is employed to remove oligonucleotides from the terminis of the modified random primer including the dideoxy nucleotide.

The TdT-extended primers are allowed to anneal to M13 mp10 virion DNA as in Example 1. AMV reverse transcriptase reaction is performed as in Example I followed by reaction with T4 DNA polymerase and T4 DNA ligase. The Example I procedures are employed for transformation and restriction endonuclease resistant mutants are selected and sequenced as summarized in Table III DNA sequence data given is for the sense (non-transcribed) strand with reference to the predicted lac transcript. Predicted amino acids for that transcript are also shown.

TABLE III

Eco RI-Resistant Mutants

| | |
|---|---|
| Starting Sequence | Eco RI<br>ATT ACG AAT TCC CGG<br>ile thr asn ser arg |
| Mutant 1 | *<br>ATT ACG GAT TCC CGG<br>asp |
| Mutant 2 | * * * * * *<br>ATT GAA CTA TCC CGG<br>glu leu |
| Mutant 3 | * * *<br>ATT ACG AAT CTC CGG<br>leu |

Sal-Resistant Mutants

TABLE III-continued

| | |
|---|---|
| Starting Sequence | Sal<br>TCC GTC GAC CTG CAG<br>ser val asp leu gln |
| Mutant 1 | * *<br>TCA ATC GAC CTG CAG<br>ser ile |
| Mutant 2 | *<br>TCC GTC AAC CTG CAG<br>asn |

Hind III-Restistant Mutants

| | |
|---|---|
| Starting Sequence | Hind III<br>CAG CCA AGC TTG GCA<br>gln pro ser leu ala |
| Mutant 1 | * * *<br>CAA CCT TGC TTG GCA<br>gln cys<br>(silent) |
| Mutant 2 | * * * *<br>CAG CCA CAT ATG GCA<br>his met |
| Mutant 3 | *<br>CAG CCA AGG TTG GCA<br>arg |

* change (substitution)
+ change due to insertion
− Change due to deletion
o cannot distinguish between "*", "+", or "−"

EXAMPLE IV

The method is used for in vitro mutagenesis of the DNA fragment of the M13 mp8 polylinker with Eco RI-Bgl II generated termini which contains the majority of the lac Z alpha complementation gene fragment using lac Z alpha complementation gene fragment of the M13 mp8 polylinker with Eco RI-Bgl II generated termini using RNA ligase for the extension of the random primers.

M13 mp8 RF is cleaved at the Eco RI and Bgl II sites to yield an approximately 800 base duplex fragment which includes most of the lac Z alpha complementation gene fragment, gene II of M13, and the mp 8 polylinker which contains the same 66 base sequence used in Example III and identified in Table A. The fragment with Eco RI-Bgl II generated termini is transferred into the polylinker of an SP6 transcription system (New England Nuclear, Boston Mass.) cleaved with Eco RI and Bam HI such that the sequences complementary to the Eco RI site are at the 3' terminus of the RNA transcribed by the SP6 system. SP6 transcribed RNA is cleaved by brief alkali digestion to nick the RNA approximately one time to yield random RNA primers.

A mixture of 4 and 5 base random DNA oligomers are chemically synthesized. These random oligomers are joined to the random primers using RNA ligase (New England Biolabs, Beverely, Mass.) to produce modified random primers. The random primers are annealed to mp8 virion DNA and AMV RT is used as in Example I to biologically fix mutations resulting from mismatched bases due to the random oligomers.

The resulting solution is dialysed against pure H₂O and heated briefly to 70° C. to dissociate the liner molecules composed of RNA and donor DNA from the circular virion template. The liner molecules are separated from virion DNA on a short agarose column selecting fragments which run faster then the virion DNA. A reverse sequencing primer 5'-CAG-GAAACAGCTATGAC-3' (Pharmecia P-L Biochemicals, Piscataway, N.J.) is annealed to the liner molecules and polymerization with AMV RT in the presence of the four deoxyribonucleoside triphosphates to produce a complementary DNA strand to the liner molecule. The complementary strand is annealed to cleaved ECO RI cleaved and dissociated M13 mp 2 RF. M13 is repaired using T4 polymerase and T4 ligase as in Example I and the same procedures are used for transformation and selection with restriction endonucleases as set forth in Table IV. Table IV shows DNA sequence data for the sense strand (non-transcribed) strand with reference to the predicted lac transcript. Predicted amino acids for that transcript are also shown.

TABLE IV

| Bam HI-Resistant Mutants | |
|---|---|
| Starting Sequence | Bam HI<br>CGG GGA TCC GTC<br>arg  gly  ser  val |
| Mutant 1 | * * *<br>CGG ATC TCC GTC<br>ile |
| Mutant 2 | * * * *<br>CGG GGA TCT AAC<br>asn<br>(silent) |
| Mutant 3 | * * *<br>CGG GGA CAT GTC<br>his |

| Pst I-Resistant Mutants | |
|---|---|
| Starting Sequence | Pst I<br>GAC CTG CAG CCA<br>asp  leu  gln  pro |
| Mutant 1 | * * *<br>GAG GGG CAG CCA<br>glu  gly |
| Mutant 2 | * * *<br>GAC AAC CAG CCA<br>asn |
| Mutant 3 | * *<br>GAG CTT CAG CCA<br>glu<br>(silent) |

* change (substitution)
+ change due to insertion
− Change due to deletion
o cannot distinguish between "*", "+", or "−"

EXAMPLE V

The method is employed for random in vitro mutagenesis of the E. Coli lac I gene cloned in a lambda vector.

Lac I RNA is produced in an SP6 transcription system into which the lac I gene has been transferred. The lac I RNA produced is annealed to the lambda vector, Charon 2 (containing lac sequences). The annealing with RNA is performed at 55° C. for 3 hours with the concentration of lambda DNA being 200 μg/μl and the concentration of lac I RNA being 50 μg/μl in an 80% formamide buffer containing 0.1M Pipes, pH 6.5, 500 mM Nacl, and 2 mM EDTA. The solution is then cooled to 45° C. over another 3 hours.

The solution containing the lambda DNA with annealed RNA is diluted 30-fold into an S1 digestion buffer containing 280 mM NaCl, 30 mM sodium acetate, pH 4.8, and 4.5 mM zinc acetate. The buffer is cooled to 10° C. and 0.01 unit/ml nuclease S1 (Sigma, St. Louis, Mo.) is added and the reaction is continued for 15 minutes at 10° C. EDTA to 10 mM is added to stop digestion and a phenol-chloroform extraction followed by a chloroform extraction is performed to remove the Nuclease S1. 100 μl 2.5M ammonium acetate, pH 8.0, and 450 μl isopropanol are then added to the aqueous phase to precipitate the DNA.

The aqueous phase containing ammonium acetate and isopropanol is frozen by placing the solution contained in a 30 ml Corex (Corning) tube in powdered dry ice and then centrifuging at 0° for 60 minutes in a SS 34 rotor (Sorval) at 10,000 rpm. The supernatent solution is aspirated and the pellet is rinsed in cold 70% ethanol and is dryed to removed ethanol but not all of the water. A buffer is added for Exo III digestion as described in Example I so that the DNA has a concentration of 150 μg/μl when resuspended. The pellet under buffer is allowed to sit at 4.0° C. for 16 hours with no mixing. It is warmed to 65° C. for 10 minutes, is gently mixed, and is allowed to sit at 4° C. for an additional 24 hours. The tube is again warmed to 65° C. for 10 minutes, is gently mixed, and is cooled to 23° C. 1000 units of Exo III are added and digestion is continued at 23° C. and 10 aliquots are removed over a 10 minute period and EDTA to 20 mM is added to each aliquot to terminate Exo III digestion. Phenol-chloroform extraction followed by chloroform extraction and performed and sodium acetate to 0.3M and two parts by volume ethanol is added. The aqueous phase is frozen on dry ice as before. Centrifugation and resuspension is performed as before but into a buffer for TdT reaction as described in Example I with 1.0 mM CoCl₂ is substituted for the 10.0 mM MgCl₂. 1000 units/ml of terminal transferase is employed to add a planned 3-4 nucleotides based on a calibration in the presence of Co²⁺ performed with a sequencing primer annealed to M13 virion DNA.

A phenol-chloroform extraction followed by chloroform extraction and an ethanol precipitation is performed and the precipitate is resuspended in Hepes buffer as described in Example I.

Biological fixation is performed as in Example I except that T4 DNA polymerization is not used. Into the Hepes buffer 50 units/ml T4 DNA ligase and 1000 units/ml AMV RT, and 200 μM rATP and the concentrations of deoxynucleotides as in Example I are added and the solution is incubated for 2 hours at 37° C. Phenol-chloroform extraction followed by chloroform extraction are performed and sodium acetate to 0.3M and two parts by volume ethanol is added. The aqueous phase is frozen on dry ice as described previously. Centrifugation and resuspension is performed as before but into 10 mM TRIS base, 5 mM MgCl₂ to result in a DNA concentration of 500 μg/ml.

In vitro packaging is performed with a lambda in vitro packaging kit available from Amersham, Arlington Heights, Ill. Following packaging, E. Coli K12 which is Δ-lac in a liquid medium is infected with the resulting lambda particles, and is used to form a lawn in a medium containing XGAL and IPTG and in a medium containing XGAL without IPTG. Mutants having the i$^s$ phenotype are identified by colorless plaques or pale blue plaques on XGAL and IPTG indicating that the inducer IPTG fails to release the product of the lac I gene from the operator and allow the expression of the β-galactosidase which cleaves the XGAL substrate. Mutants having the i$^-$ phenotype are identified as producing blue plaques even in the absence of the inducer IPTG and indicate the lack of repression and constitutive expression of β-galactosidase which cleaves the substrate XGAL. Mutants identified are shown in Table V. DNA sequence data given is for the sense (non-transcribed) strand with reference to the predicted lac transcript. Predicted amino acids for that transcript are also shown.

To confirm the sequence and the i$^s$ phenotype of Mutant 2 and to further amplify the sequence, a sequence containing the mutation is chemically synthesized and is used to mutagenize the wild type lac I gene cloned in M13 according to the oligonucleotide-mediated mutagenesis procedures described in T. Kunkel, A Rapid and Efficient Site-Specific Mutagenesis without Phenotypic Selection, *Proc. Natl. Acad. Sci.*, 82: 488–492 (1985). The following chemically synthesized sequence is used:

GTGGAAGCTGCCTATACTAATGTTCCGG

Of the plaques produced by this method, 12 are selected and sequenced. Ten contain the wild type sequence and produce intense blue plaques and two contain the same sequence as Mutant 2 and both give a paler blue color in the presence of IPTG and XGAL. Sequencing confirms that the same mutation is produced as in Mutant 2 shown in Table V.

TABLE V

| | i$^s$ Phenotype | | | | | | |
|---|---|---|---|---|---|---|---|
| Starting Sequence | 80 | | | 84 | | | |
| | GTC | GCG | GCG | ATT | AAA | TCT | CGC GCC |
| | val | ala | ala | ile | lys | ser | arg ala |
| Mutant 1 | | | | * ** | | | |
| | GTC | GCG | GCG | ATC | CTA | TCT | CGC GCC |
| | | | | |⎯⎯⎯| leu | | |
| | | | | (silent) | | | |
| Starting Sequence | 140 | | | | | | |
| | GCT | GCC | TGC | ACT | AAT | | |
| | ala | ala | cys | thr | asn | | |
| Mutant 2 | | | * * | | | | |
| | GCT | GCC | TAT | ACT | AAT | | |
| | | | tyr | | | | |
| | i-Phenotype | | | | | | |
| Starting Sequence | 5 | | | | | | |
| | AAA | CCA | GTA | ACG | TTA | TAC | |
| | lys | pro | val | thr | leu | tyr | |
| Mutant 3 | | | | * * * | | | |
| | AAA | CCA | GTA | CAA | TTA | TAC | |
| | | | | gln | | | |

TABLE V-continued

| | 45 | | | | |
|---|---|---|---|---|---|
| Starting Sequence | GCG | GAG | CTG | AAT | TAC |
| | aln | glu | leu | asn | tyr |
| Mutant 4 | | * *** | | | |
| | GCG | GAA | AGC | AAT | TAC |
| | |⎯⎯⎯| ser | | | |
| | (silent) | | | | |

Only regions showing mutations are displayed in this table.
* change (substitution)
+ change due to insertion
− Change due to deletion
o cannot distinguish between "*", "+", or "−"

The foregoing examples illustrate that the method of the present invention has the capability for producing substitution mutations of codon length or more at a single randomly-located region in a target sequence. The method efficiently provides a population of mutants and is useful in protein engineering and wide variety of biological studies.

Although particular embodiments of the present invention have been described in the foregoing description and examples, it will be understood that the invention is capable of numerous modifications without departing from the spirit of the invention as set forth in the appended claims.

What is claimed is:

1. An in vitro method fo mutagenesis of a target DNA sequence comprising:
   producing a supply of a template for the target sequence;
   producing random primers having differing 3'—OH termini with each having a region complementary to said template adjacent to said 3'—OH termini;
   extending said random primers randomly from said 3'—OH termini by at least two deoxynucleotides to produce modified random primers, at least some of which have at least one nucleotide which is mismatched with respect to the template; wherein said step of extending said random primers is accomplished by random addition of nucleotides with terminal transferase in the presence of the four nucleotides at appropriate concentrations so that the probability of addition of any of the four nucleotides is approximately equal at any one site,
   employing said modified random primers as primers for DNA polymerization and polymerizing DNA along said template to form at least some mutagenized DNA containing double stranded regions each having a newly-polymerized strand with at least one nucleotide which is mismatched with respect to the template;
   transferring at least nucleic acid containing the equivalent sequence information of said newly-polymerized strands of said mutagenized DNA into organisms to cause at least some of said nucleic acid to be replicated in said host organisms to produce mutant DNA sequences;
   growing said host organisms to produce a population of clones containing a variety of mutant DNA sequences;
   selecting at least one clone from the population having selected characteristics; and
   growing host organisms containing mutant DNA sequences of said selected clones to amplify said sequences.

2. The method of claim 1 wherein the addition of nucleotides of said random primers with terminal transferase is performed such that said addition is controlled kinetically to add a selected number of nucleotides.

3. The method of claim 1 wherein the addition of nucleotides to said random primers is controlled by the presence of dideoxynucleoside triphosphates in sufficient concentration which cause incorporation of dideoxynucleotides to stop addition at a selected number of nucleotides then digesting with an exonuclease to remove dideoxynucleotides to produce said modified random primers.

4. An in vitro method for mutagenesis of a target DNA sequence comprising:
   producing a supply of a template for the target sequence;
   producing random primers having differing 3'—OH termini with each having a region complementary to said template adjacent to said 3'—OH termini;
   extending said random primers randomly from said 3'—OH termini by at least two deoxynucleotides to produce modified random primers, at least some of which have at least one nucleotide which is mismatched with respect to the template; wherein said step of extending said random primers is accomplished by the addition of random oligonucleotides with RNA ligase, said oligonucleotides having a predetermined length range,
   employing said modified random primers as primers for DNA polymerization and polymerizing DNA along said template to form at least some mutagenized DNA containing double stranded regions each having a newly-polymerized strand with at least one nucleotide which is mismatched with respect to the template;
   transferring at least nucleic acid containing the equivalent sequence information of said newly-polymerized strands of said mutagenized DNA into organisms to cause at least some of said nucleic acid to be replicated in said host organisms to produce mutant DNA sequences;
   growing said host organisms to produce a population of clones containing a variety of mutant DNA sequences;
   selecting at least one clone from the population having selected characteristics; and
   growing host organisms containing mutant DNA sequences of said selected clones to amplify said sequences.

5. An in vitro method for mutagenesis of a target DNA sequence comprising:
   producing a supply of a template for the target sequence;
   producing random primers having differing 3'—OH termini with each having a region complementary to said template adjacent to said 3'—OH termini;
   extending said random primers randomly from said 3'—OH termini by at least two deoxynucleotides to produce modified random primers, at least some of which have at least one nucleotide which is mismatched with respect to the template;
   employing said modified random primers as primers for DNA polymerization and polymerizing DNA along said template to form at least some mutagenized DNA containing double stranded regions each having a newly-polymerized strand with at least one nucleotide which is mismatched with respect to the template;
   transferring at least nucleic acid containing the equivalent sequence information of said newly-polymerized strands of said mutagenized DNA into organisms to cause at least some of said nucleic acid to be replicated in said host organisms to produce mutant DNA sequences;
   growing said host organisms to produce a population of clones containing a variety of mutant DNA sequences;
   selecting at least one clone from the population having selected characteristics; and
   growing host organisms containing mutant DNA sequences of said selected clones to amplify said sequences wherein said step of growing host organisms containing mutant DNA sequence of said selected clones to amplify said sequences is accomplished by sequencing mutant DNA from said selected clone to determine sequence information descriptive of said mutant sequence, reproducing said mutant sequences based on said sequence information, transferring said reproduced mutant sequences into host organisms and growing said host organisms to produce a supply of the sequences.

6. An in vitro method for mutagenesis of a target DNA sequence comprising:
   cloning the target sequence in M13 to produce virion DNA containing an insert, said insert being a template for the sequence;
   annealing a sequencing primer to the virion DNA;
   producing random primers by polymerizing from said sequencing primer using a DNA polymerase in the presence of the four nucleoside triphosphates and controlling the polymerization of said random primers to produce differing 3'—OH termini in the template region;
   extending said random primers randomly with terminal transferase from said 3'—termini by a least two nucleotides to produce modified random primers, some of said modified random primers having at least one nucleotide which is mismatched with respect to the template;
   annealing said modified random primers to said virion DNA;
   employing said modified random primers as a primer for polymerization with reverse transcriptase in the presence of the four nucleoside triphosphates and polymerizing along said template at least partially along said virion DNA to produce at least some mutagenized DNA containing double-stranded regions each having a newly-polymerized strand which has at least one nucleotide which is mismatched with respect to the template;
   transferring at least nucleic acid containing the equivalent sequence information of said newly-polymerized strands into host organisms to cause at least some of said nucleic acid to be replicated in said host organisms to produce mutant DNA sequences;
   growing said host organisms to produce a population of clones containing a variety of mutant DNA sequences;
   selecting at least one clone from the population having selected characteristics; and
   growing host organisms containing mutant DNA sequences of said selected clones to amplify said sequences.

7. The method of claim 6 wherein said extending of said random primers with terminal transferase is performed in the presence of all four nucleotides and the addition is controlled to add a selected number of nucleotides.

8. The method of claim 7 wherein the concentration of each of the four nucleotides is such that the probability of addition of any of the four nucleotides is approximately equal at any one site.

9. The method of claim 7 wherein the dideoxynucleoside triphosphates are present in sufficient concentration to be incorporated to stop addition at a selected approximate number of nucleotides and digestion with an exonuclease to remove dideoxynucleotides is performed to produce said modified random primers.

10. The method of claim 6 wherein the step of extending said random primers is accomplished by the addition of random oligonucleotides with RNA ligase, said oligonucleotides having a predetermined length range.

11. The method of claim 6 wherein said transferring of at least nucleic acid containing the equivalent sequence information of said newly-polymerized strands into host organisms is accomplished by the steps of:
generating DNA containing the equivalent sequence information of said newly-polymerized strands; and
transferring said DNA into host organisms to produce said mutant DNA sequences.

12. The method of claim 11 wherein said steps of generating DNA containing the equivalent sequence information of said newly-polymerized strands and transferring said DNA into host organisms are accomplished by further polymerizing said newly-polymerized strand along said virion DNA and sealing the nick with a DNA ligase to produce M13 double-stranded DNA and transforming a competent host with said M13 double-stranded DNA under conditions which cause said newly-polymerized strands to be replicated to produce said mutant DNA sequences.

13. The method of claim 12 wherein said completing of said polymerization with a DNA polymerase is performed with T4 DNA polymerase and said sealing of the nick is accomplished with T4 DNA ligase.

14. The method of claim 11 wherein said step of generating DNA containing equivalent sequence information of said newly-polymerized strands is accomplished by dissociating said newly-polymerized strands from said virion DNA, annealing a reverse sequencing primer to said newly-polymerized strands and polymerizing complementary strands along said newly-polymerized strands employing a DNA polymerase in the presence of the four deoxynucleoside triphosphates.

15. An in vitro method for mutagenesis of a target DNA sequence comprising:
producing a supply of template for the target sequence;
producing random primers having differing 3'—OH termini with each having a region complementary to said template adjacent to said 3'—OH termini;
hybridizing said random primers to said template;
extending said random primers randomly from said 3'—OH termini by at least two deoxynucleotides to produce modified random primers, at least some of which have at least one nucleotide which is mismatched with respect to the template;
employing said modified random primers as primers for DNA polymerization and polymerizing DNA along said template to form at least some mutagenized DNA containing double stranded regions each having a newly-polymerized strand with at least one nucleotide which is mismatched with respect to the template;
transferring at least nucleic acid containing the equivalent sequence information of said newly-polymerized strands of said mutagenized DNA into organisms to cause at least some of said nucleic acid to be replicated in said host organisms to produce mutant DNA sequences;
growing said host organisms to produce a population of clones containing a variety of mutant DNA sequences; selecting at least one clone from the population having selected characteristics; and
growing host orgnisms containing mutant DNA sequences of said selected clones to amplify said sequences.

16. The method of claim 15 wherein said step of employing said modified random primers with said supply of said template as primers for polymerization along said template is accomplished with a DNA polymerase which lacks the 3' to 5' editing activity.

17. The method of claim 16 wherein said step of extending said random primers is accomplished by random addition of nucleotides with terminal transferase in the presence of at least one of the four nucleotides.

18. The method of claim 16 wherein said step of extending said random primers is accomplished by random addition of nucleotides with terminal transferase in the presence of the four nucleotides at appropriate concentrations so that the probability of addition of any of the four nucleotides is approximately equal at any one site.

19. The method of claim 18 wherein the addition of nucleotides to said random primers with terminal transferase is performed such that said addition is controlled kinetically to add a selected number of nucleotides.

20. The method of claim 18 wherein the addition of nucleotides of said random primers is controlled by the presence of dideoxynucleoside triphosphates in sufficient concentration which cause incorporation of dideoxynucleotides to stop addition at a selected number of nucleotides then digesting with an exonuclease to remove dideoxynucleotides to produce said modified random primers.

21. The method of claim 15 wherein the step of extending said random primers is accomplished by the addition of random oligonucleotides with RNA ligase, said oligonucleotides having a predetermined length range.

22. The method of claim 15 wherein said step of growing host organisms containing mutant DNA sequence of said selected clones to amplify said sequences is accomplished by sequencing mutant DNA from said selected clone to determine sequence information descriptive of said mutant sequence, reproducing said mutant sequences based on said sequence information, transferring said reproduced mutant sequences into host organisms and growing said host organisms to produce a supply of the sequences.

* * * * *

UNITED STATES PATENT AND TRADEMARK OFFICE
CERTIFICATE OF CORRECTION

PATENT NO. : 4,959,312
DATED : September 25, 1990
INVENTOR(S) : Karl M. Sirotkin It is certified that error appears in the above-identified patent and that said Letters Patent is hereby corrected as shown below:

Column 3, line 66, "corresponding" should be --containing--.

Column 6, line 9, after conveniently insert --generated--.

Column 8, line 9, after template delete "." and insert --,--.

Column 10, line 17, after T4 insert --DNA--.

Column 12, line 45, "Fragment" should be --fragment--.

Column 14, line 21, after (BRL) insert --as--.

In Table A, Example II, after Bam insert --HI--.

UNITED STATES PATENT AND TRADEMARK OFFICE
CERTIFICATE OF CORRECTION

PATENT NO.  : 4,959,312

DATED       : September 25, 1990

INVENTOR(S) : Karl M. Sirotkin

It is certified that error appears in the above-identified patent and that said Letters Patent is hereby corrected as shown below:

Column 15, Table I, under BamH1-Resistant Mutants, Mutant 5, before AAT delete "CGG" and insert --GGG--.

Column 24, line 30, Claim 1, "fo" should be --for--.

Column 25, line 2, "of" should be --to--.

Column 26, line 39, after 3'- insert --OH--.

Signed and Sealed this

Twenty-eighth Day of April, 1992

Attest:

HARRY F. MANBECK, JR.

*Attesting Officer*          *Commissioner of Patents and Trademarks*